United States Patent [19]

Swope et al.

[11] Patent Number: 5,002,392
[45] Date of Patent: Mar. 26, 1991

[54] MULTICHANNEL OPTICAL MONITORING SYSTEM

[75] Inventors: C. Hermas Swope, Raleigh; John G. Link, Durham; Douglas G. Haugen, Durham; Joseph G. Karp, Durham, all of N.C.

[73] Assignee: Akzo N.V., Arnhem, Netherlands

[21] Appl. No.: 443,952

[22] Filed: Dec. 1, 1989

[51] Int. Cl.[5] ............................ G01J 3/08; G01J 3/42
[52] U.S. Cl. ..................................... 356/328; 356/330
[58] Field of Search ............... 356/310, 319, 320, 323, 356/325, 326, 328, 330

[56] References Cited

U.S. PATENT DOCUMENTS

| 4,685,801 | 8/1987 | Minekane | 356/328 |
| 4,718,762 | 1/1988 | Wiget et al. | 356/328 |

FOREIGN PATENT DOCUMENTS

| 159289 | 12/1979 | Japan | 356/320 |

Primary Examiner—F. L. Evans
Attorney, Agent, or Firm—Spencer & Frank

[57] ABSTRACT

A multichannel optical monitoring system for monitoring the spectral transmission of a plurality of samples. A plurality of light beams are generated and a plurality of optical monitoring stations are arranged along a pathway, each station having an optical path formed by one of the light beams transverse to the pathway and along which optical characteristics are monitored. A drive mechanism moves a plurality of reaction wells, each containing a reaction volume, along the pathway from station to station so that respective reaction volumes dwell periodically in each optical path for transmitting a respective one of the light beams. A diffraction grating is arranged for diffracting the beams transmitted by respective ones of the reaction volumes. The diffracted beams are focussed and at least one array of photodetectors is positioned for receiving the diffracted and focussed beams for producing electrical signals representing the spectral content of the diffracted beams. An electronic circuit detects the electrical signals of the array, which signals may be stored for further processing and evaluation.

30 Claims, 9 Drawing Sheets

MULTICHANNEL OPTICAL MONITORING SYSTEM

BACKGROUND OF THE INVENTION

The present invention relates to an optical analyzer for chemical reactions for use in performing, for example, analyses of hemostasis, thrombosis and infectious diseases.

Optical instruments are known which measure coagulation time of a patient's blood. Such instruments generally comprise a lamp and a detector. A sample of blood plasma and a clotting reagent are dispensed into the reaction well of a cuvette and a light beam from the lamp is directed through a cuvette to the detector. The voltage of the detector is read by a computer and the data are mathematically processed to determine the time at which the clot forms.

Automated chemical analyzers have been developed which can automatically perform analyses on multiple patient samples without operator intervention. In one such machine developed by the assignee of the present application, sample volume containers with bar code information on the side identifying the sample and the test to be performed by the analyzer are loaded into a temperature controlled compartment, which also stores reagents and other additives under temperature control. The samples are automatically dispensed into reaction wells of cuvettes, and reagents and possibly other additives are automatically combined with the test samples according to the programmed test read from the bar code on the sample container. The reaction wells now containing a reaction volume composed of a test sample and additives are transported to an optical analyzer which monitors changes in optical characteristics of the reaction volume, which changes are processed and evaluated according to the particular test being performed. This machine is capable of performing tests on hundreds of patient samples without intervention of the operator once the sample containers are loaded into the temperature controlled compartment. A sample handling system of the type described above is disclosed in greater detail in copending and concurrently filed U.S. Pat. application Ser. No. 07/443,951, to Hulette et al, entitled "Sample Handling System For An Optical Monitoring System," and a specially designed cuvette and linear drive mechanism therefor for use in the sample handling system is disclosed in greater detail in copending and concurrently filed U.S Patent Application Serial No. 07/443,956 to Karp et al, entitled "Cuvette And Linear Drive Mechanism Therefor," both of which applications are assigned to the assignee of the present application. The disclosures of both of the foregoing applications are incorporated herein by reference.

In order to handle the high throughput of such a machine, and to provide the versatility to perform a variety of tests without operator intervention, it was necessary to develop an improved optical analyzer that could, among other things, simultaneously optically monitor a plurality of reaction volumes over an extended period of time and with respect to a wide spectral range so that the machine could be programmed to perform a wide variety of tests, including tests yet to be developed.

SUMMARY OF THE INVENTION

It is therefore an object of the invention to provide a multichannel optical analyzer that can substantially simultaneously monitor a plurality of reaction volumes over a wide spectral range.

It is a further object of the invention to provide a multichannel optical analyzer that can handle a high throughput of patient samples.

It is yet another object of the invention to provide a multichannel optical analyzer that has versatility and adaptability, and reliable automation.

The above and other objects are accomplished according to the invention by the provision of multichannel optical monitoring system for monitoring the spectral transmission of a plurality of samples, including: a beam generator for generating a plurality of light beams; a plurality of optical monitoring stations arranged along a pathway, each station having an optical path formed by one of the light beams transverse to the pathway and along which optical characteristics are monitored; drive device for moving a plurality of reaction wells, each containing a reaction volume, along the pathway from station to station s that respective reaction volumes dwell periodically in each optical path for transmitting a respective one of the light beams; a diffraction device arranged for diffracting the beams transmitted by respective ones of the reaction volumes; focusing lenses following the diffraction device for focussing the diffracted beams; at least one array of photodetectors positioned for receiving the diffracted and focussed beams for producing electrical signals representing the spectral content of the diffracted beams; and an electronic circuit for detecting the electrical signals of the at least one array.

In a preferred embodiment the pathway is linear and a shutter is provided for sequentially passing the light beams transmitted by the reaction volumes at the plurality of optical monitoring stations.

Desirably, a plurality of detector arrays will be provided. For example in one implementation of the optical monitoring system according to the invention, four detector arrays are used, and twenty reaction volumes are substantially simultaneously monitored. In such an arrangement, the light from each group of five reaction volumes is focussed on a respective one of the arrays. The shutter sequentially passes the light beams transmitted by each group of reaction volumes so that only one light beam transmitted by each group of samples (i.e. in this example, one light beam in five) is allowed to reach its respective array at any one time.

According to a further feature of the invention, the diffraction grating comprises a high dispersion, high efficiency holographic diffraction grating.

According to a further aspect of the invention a method is provided for monitoring the spectral transmission of a plurality of samples, including: generating a plurality of light beams; arranging a plurality of optical monitoring stations along a pathway, each station having an optical path formed by on of the light beams transverse to the pathway and along which optical characteristics are monitored; moving a plurality of reaction wells, each containing a reaction volume, along the pathway from station to station so that respective reaction volumes dwell periodically in each optical path for transmitting a respective one of the light beams; diffracting the beams transmitted by respective ones of the reaction volumes; focussing the diffracted beams; converting the diffracted and focussed beams to electrical signals representing the spectral content of the diffracted beams; and detecting the electrical signals.

In a preferred embodiment of the method according to the invention, there is further included the step of sequentially passing the light beams transmitted by the reaction volumes at the plurality of optical monitoring stations.

Various other features and advantages of the invention will become apparent from the detailed description below taken in conjunction with the accompanying drawings and the appended claims.

DETAILED DESCRIPTION OF THE PREFERRED EMBODIMENT

Figures 1, 3, 4:
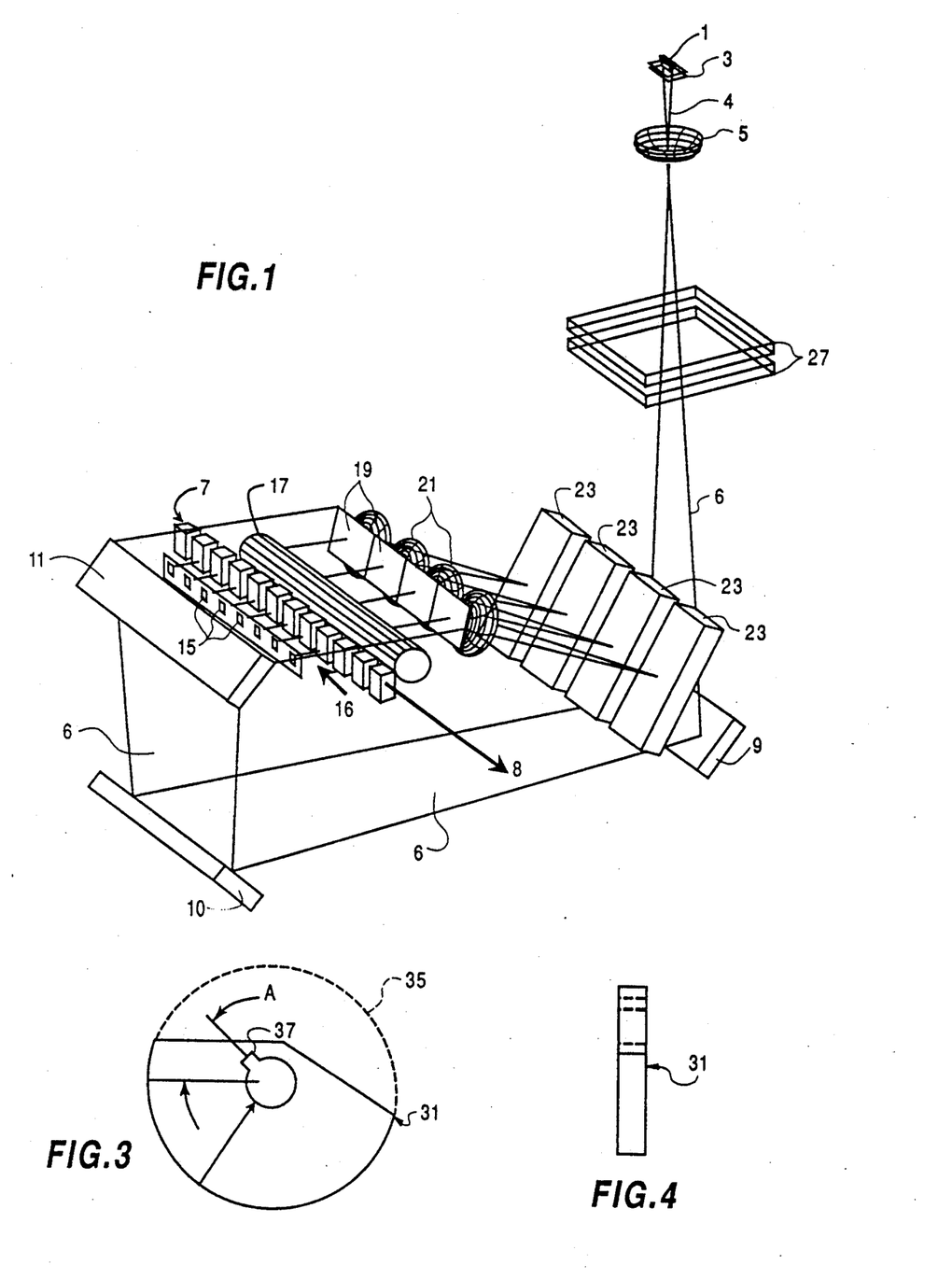
FIG. 1 is a schematic showing an embodiment of the optical monitoring system according to the invention.
FIG. 3 is a side elevational view of one of the rotating cam elements in the shutter of FIG. 2.
FIG. 4 is a side elevational view of the cam in FIG. 3.

Referring to FIG. 1, there is shown a schematic of an optical monitoring system according to the invention. A broad band spectral light source 1, such as a tungsten-halogen lamp or a Xenon lamp, which may include a diffuser (not shown), projects light toward a slit forming device 3 (hereinafter referred to as slit 3) which passes a beam 4 having the pattern of a slit. A short focal length collimator 5 follows the slit and is used to project the slit shaped beam 4 to infinity, thereby forming a slowly diverging beam 6. The slit length and collimator are chosen so that at a reasonable distance beam 6 has diverged to cover a plurality of reaction wells 7 containing a reaction volume to be optically monitored. Slit 3 may be formed., for example, of a stainless steel substrate 0.013 mm thick having an air slit width of 100 $\mu$m and length of 5.0 mm. Collimator 5 may be an Edmund Scientific Co. Achromat No. J32,319, which has a focal length of 35 mm, diameter of 25 mm, center thickness of 13.50 mm and which is antireflection coated with $\frac{1}{4}$ wavelength $MgF_2$.

For purposes of making the optical system compact, beam 6 may be folded a number of times as shown by mirrors 9, 10 and 11. Prior to reaching reaction wells 7, beam 6 is intercepted by a mask 13 having a plurality of openings 15 for dividing beam 6 into a plurality of separate beams 16, corresponding to the number of reaction wells 7 to be monitored. The divided beams 16 are sized and spaced so that each beam passes through the desired portion of just one of the reaction wells 7. Reaction wells 7 may be filled with a reaction volume to be optically monitored by a sampling handling system as described, for example, in the aforementioned copending U.S. Pat. application Ser. No. 07/443,751, Hulette et al., and are incrementally moved in the direction of arrow 8 from station to station (each station corresponding to the optical path of a respective one of the diverging beams), for example by the linear drive mechanism disclosed in the aforementioned copending U.S. Pat. application Ser. No. 07/443,956, to Karp et al.

For purposes of the following description, it will be assumed that 20 reaction wells are to be simultaneously optically monitored, although, for ease of illustration FIG. 1 shows only 8 openings 15 in mask 13 creating 8 beams for monitoring 8 reaction wells. Obviously, the number of reaction wells to be monitored could vary depending on particular design requirements. Mask 13 may be a metal substrate one sixteenth of an inch thick with, in the example being used, 20 openings sized, for example 0.0675 by 0.0715 inches, and spaced 0.2411 inches.

After each of beams 16 pass through a respective reaction well 7, beams 16 are intercepted by a rotating shutter 17, described in greater detail below in connection with FIGS. 2 to 5, for sequentially passing the beams transmitted by the reaction volumes in reaction wells 7. The beams passing through shutter 17 are diffracted by diffraction gratings 19. In the present example, four diffraction gratings are positioned so that each group of sequentially passed five beams is diffracted by a respective one of the four diffraction gratings 19. Diffraction gratings 19 are preferably high dispersion, high efficiency transmission holographic diffraction gratings having a pitch of 0.8744 $\mu$m. A plurality of focussing lenses 21, one following each diffraction grating, focus the diffracted light onto a corresponding array 23 of linearly arranged photodetectors. Photodetector arrays 23 are oriented so that the spectrum of the diffracted beams falls across the linearly arranged photodetector elements and the optics of the system are such that a central element of each array 23 is an optical conjugate of slit 3. In a preferred embodiment, each photodetector array includes 35 identical photodiodes each covering a spectral range of 390 nm to 690 nm with a spectral resolution of 10 nm. Photodiode arrays of this type are commercially available, for example, from the Hamamatsu Company of Japan under Part No. S 2317–35Q. Preferably, one or more filters 27 are located, for example between collimator 5 and mirror 9, for balancing the spectral response of the photodiode detectors with the spectral output of light source 1.

Photodiode arrays 23 each develop electrical signals corresponding to the spectral distribution falling on the array. Arrays 23 are connected to scanning and recording electronics (see FIG. 6) which sequentially scan the photodiodes for converting the electrical signals to digital signals and storing the digital signals in a computer memory for further processing and evaluation.

Figure 2:
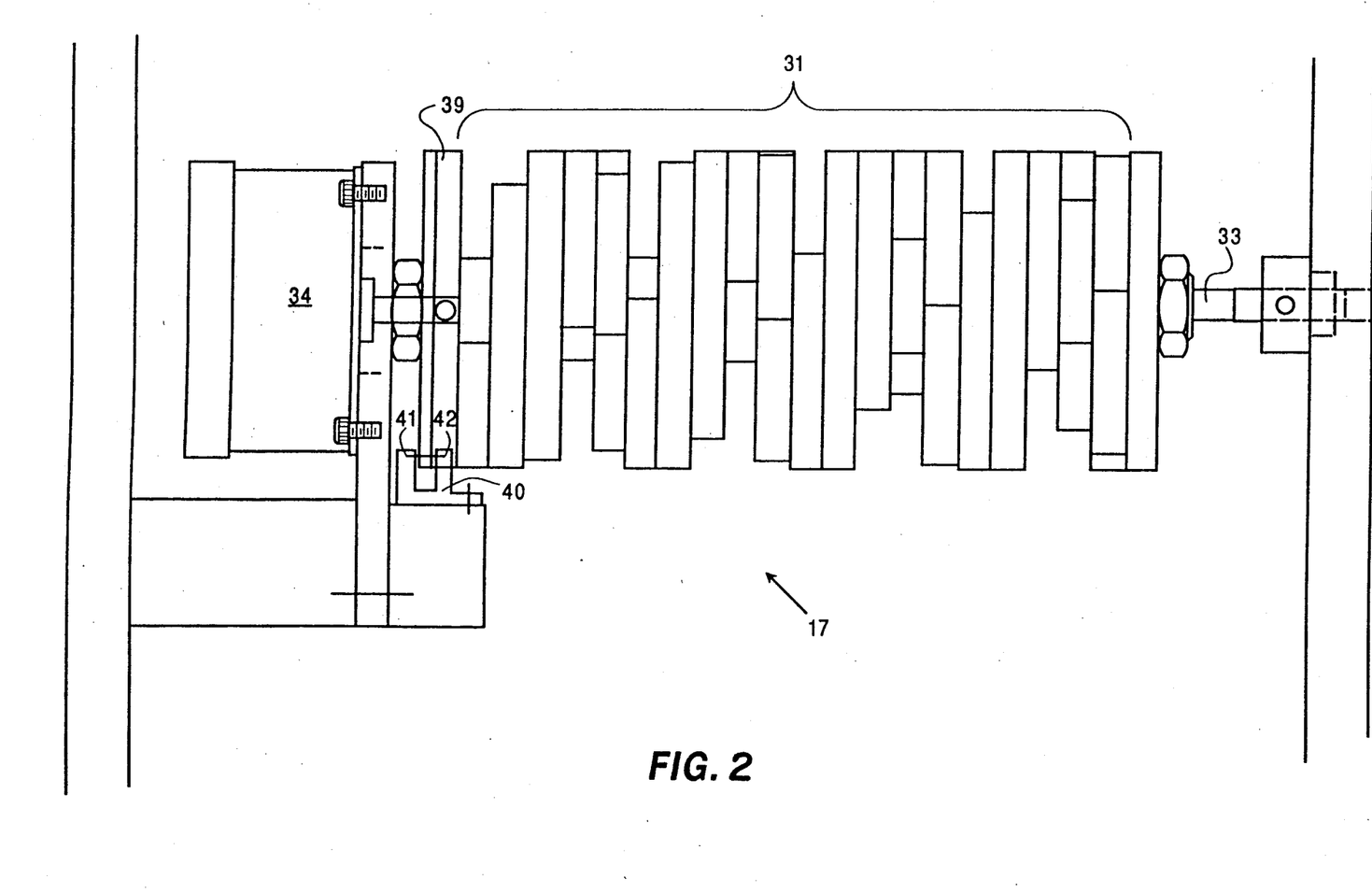
FIG. 2 is a front elevational view of an embodiment of a rotating shutter that may be used in the system shown in FIG. 1.

FIGS. 2 to 4 illustrate preferred embodiment for rotating shutter 17, it being understood that other configurations for shutter 17 are possible within the scope of the invention. As shown in FIG. 2, rotating shutter 17 comprises a number of cam elements 31 mounted on a shaft 33, driven by a motor 34. FIG. 2 shows 20 cam elements 31, corresponding to the example of 20 optical stations being used in this description. Cam elements 31 are each arranged in the optical monitoring system so that they are aligned with a respective one of beams 16 passed through windows 15 of mask 13 shown in FIG. 1. Each cam element 31 has a sector removed so that upon rotation of shutter 17 each of the beams 16 is either blocked or passed depending on the rotational position of the respective cam element. Referring to FIGS. 3 and 4, cam elements 31 each have the same size sector 35 removed, and differ only in the angular placement of a keyway 37 which engages an axial key (not shown) on shaft 33. The angular placement of keyway 37 relative to cutout 35 on respective cam elements 31 determines the timing sequence in which beams 16 are passed to detector arrays 23. In one specific implementation of shutter 17 for use in an optical monitoring system of the type shown in FIG. 1 with 20 stations, cam elements 31 have a diameter of 2.52 inches, a width of 0.265 inches, a 210.5° sector removed, and a placement angle A° of the respective keyways as shown in the following table:

| Cam Element No. | A° | Cam Element No. | A° |
| --- | --- | --- | --- |
| 1 | 0.00 | 11 | 32.00 |
| 2 | 64.00 | 12 | 96.00 |
| 3 | 128.00 | 13 | 160.00 |
| 4 | 192.00 | 14 | 224.00 |
| 5 | 256.00 | 15 | 288.00 |
| 6 | 16.00 | 16 | 48.00 |
| 7 | 80.00 | 17 | 112.00 |
| 8 | 144.00 | 18 | 176.00 |
| 9 | 208.00 | 19 | 240.00 |
| 10 | 272.00 | 20 | 304.00 |

Figure 5:
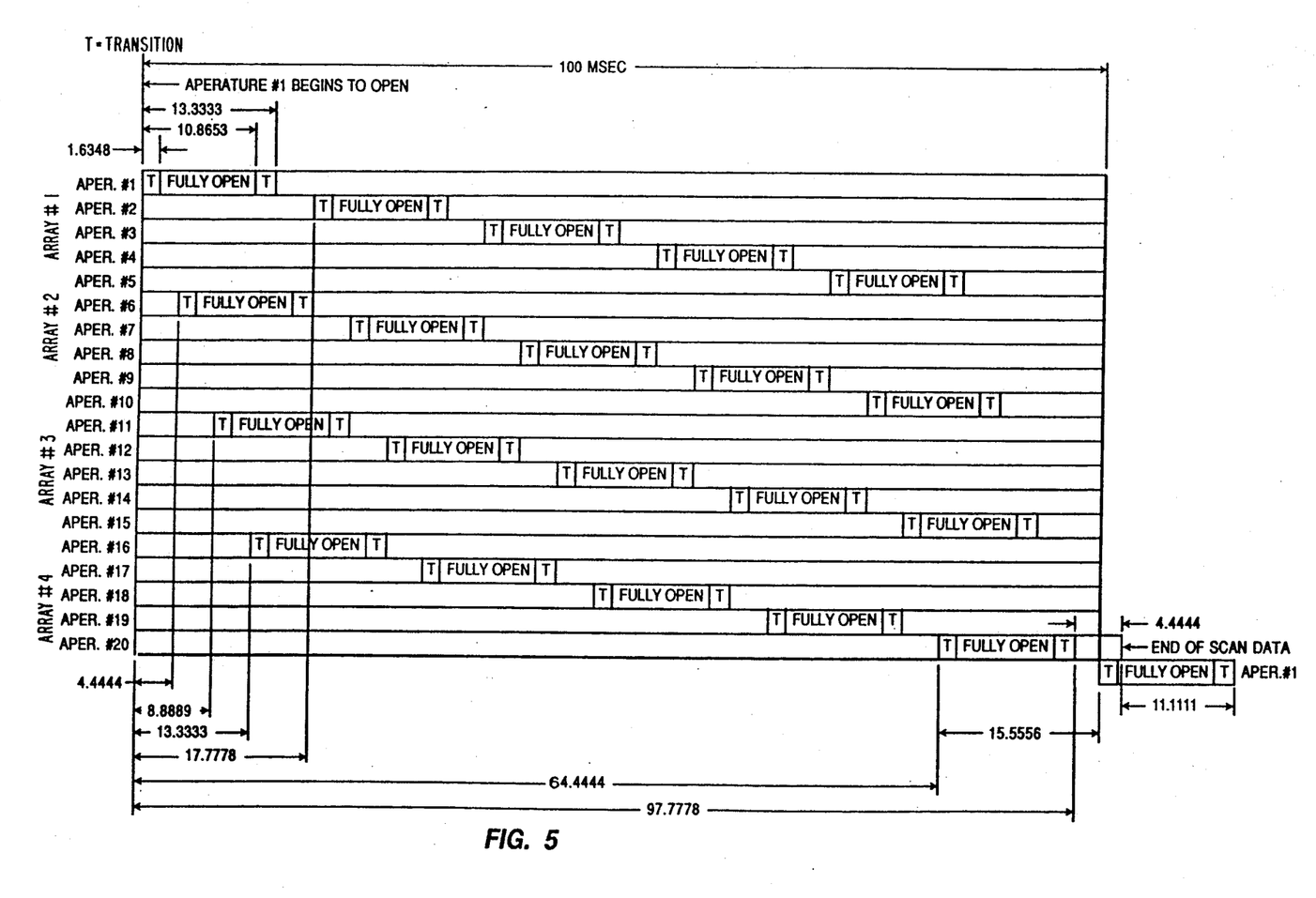
FIG. 5 is a timing diagram for the rotating shutter in FIG. 2 according to on embodiment of the invention.

A rotating shutter configured as described above and rotating at 10 revolutions per second produces a timing diagram as shown in FIG. 5. Each cam element 31 constitutes a shutter element and remains fully open for 10.0653 milliseconds, with an opening and closing transition time T on either end of the fully open position of 1.634 milliseconds seconds. At the conclusion of the closing transition time T of each cam element, the detector array 23 on which the spectral distribution from that cam element is projected is electronically scanned and electrical signals representing the spectral distribution across the array are recorded.

Referring again to FIG. 2, rotating shutter 17 is provided with a timing disc 39 having a sector removed (not shown) for providing a synchronizing signal for synchronizing the electronic scanning of the arrays. More specifically, there is additionally provided an opto-electronic circuit 40, including an optical transmitter 41 which directs a light beam toward an optical receiver 42. This beam is interrupted by disc 39 except for the time when the sector removed from disc 39 is in the optical path between optical transmitter 41 and optical receiver 42. An electrical synchronization signal developed by optical receiver 42 during reception of the beam from optical transmitter 41 is fed to the electronic scanner shown in FIG. 6.

Figure 6:
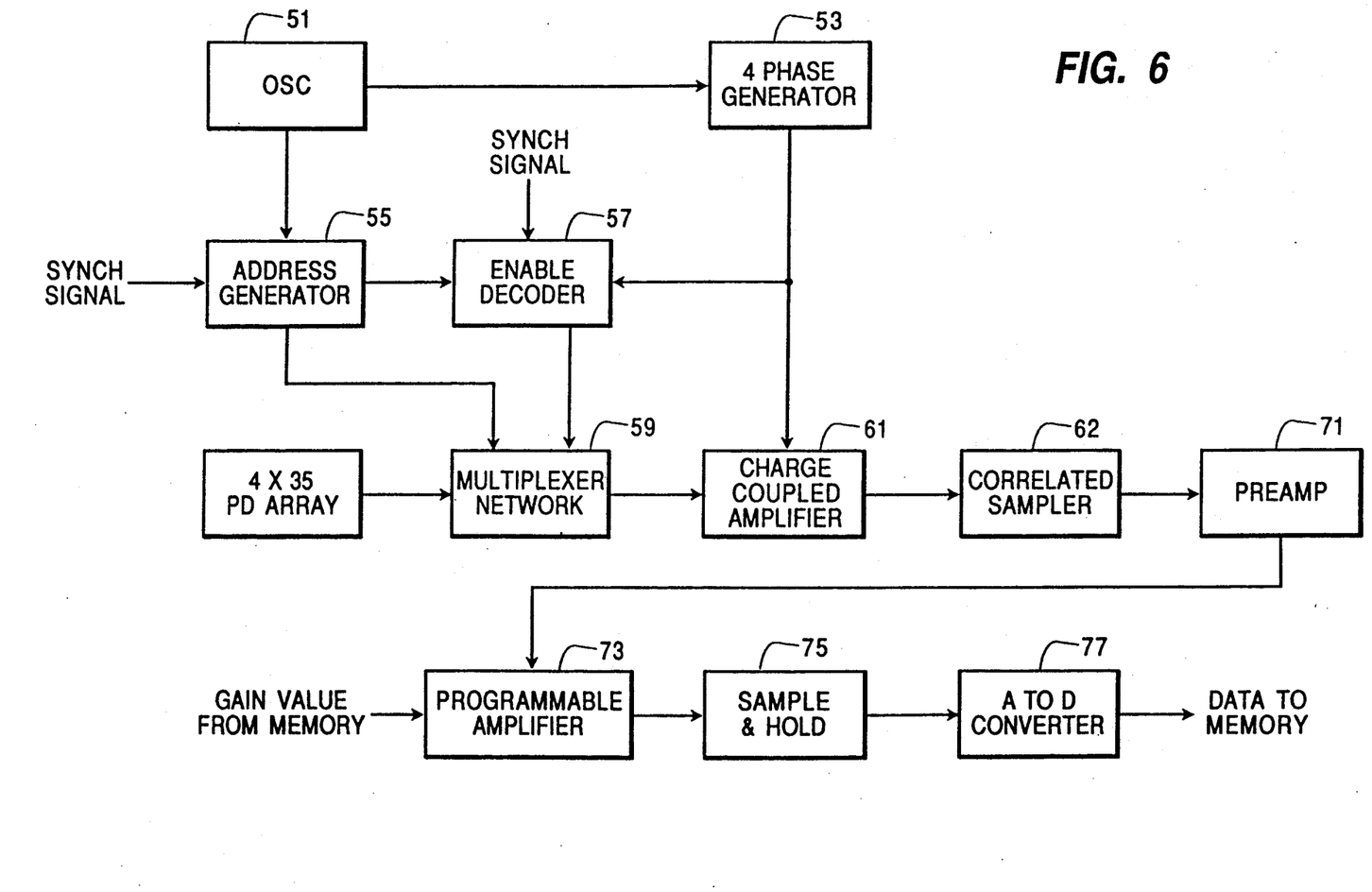
FIG. 6 is a block circuit diagram of an electronic scanner for the photodiode arrays shown in FIG. 1.

FIG. 6 shows a block circuit diagram of an electronic scanner for scanning the four photodiode arrays 23. As previously discussed, each photodiode array 23 contains 35 photodiode elements; however, for purposes of the timing in the scanner, each photodiode array 23 is considered to have 40 virtual photodiodes, so that there are a total of 160 virtual photodiode elements to be scanned. As will be discussed, the scanner is connected for scanning the photodiodes sequentially in twenty blocks of 8 photodiodes per block.

The scanner is based on the charge storage mode of operation. In the charge storage mode of operation, a photodiode integrates the photon to electrical conversion over a predetermined time period. A charge coupled amplifier replicates the integrated electrical signal. More precisely, as light strikes each of the photodiode surfaces of photodiode array 23 (FIG. 1) electrons are driven out of the p-n junction by photons. The charge stored in the parasitic capacitance of the diode becomes depleted of charge carriers with increasing light. In the charge storage mode of operation, the amount of charge lost is determined by measuring how much charge it takes to fully (or nearly fully) recharge the photodiode element. (For more discussion on the charge storage mode of operation, see, for example, Hamamatsu Photonics K.K., *Characteristics and Use of PCD Linear Image Sensors*, Technical Bulletin No. SD-03.

The charge storage mode of operation is preferred in an environment in which hundreds of low level optical signals must be evaluated at high speeds, and wherein the cost and space required for a separate amplifier for each photodiode become prohibitive.

With the above background in mind, FIG. 6 will now be described in detail.

Referring to FIG. 6, there is shown a free running oscillator 51 having a basic frequency of 18.432 MHz which is subdivided down to 144 KHz for driving a four phase generator 53. Four phase generator 53 includes a frequency divider which produces a 36 KHz clock signal and a decoder which receives the 36 KHz clock signal and produces four sequential pulses, hereinafter referred to as phases P1, P2, P3 and P4, on separate lines which are used as the basic timing signals for the scanner. Each four cycles of the 36 KHz clock signal cause the scanner to go through one complete scanning cycle in which a single photodiode element of a photodiode array 23 is read.

The 144 KHz signal from oscillator 51 is additionally used to drive an address generator 55 which also receives the synchronization signal from opto-electronic circuit 40 (FIG. 2). Address generator 55 includes an eight bit binary address, the lower three bits representing the address of one of the photodiode elements in each group of 8 photodiode elements. An enable decoder 57 is connected for receiving the upper five bits of address generator 55, phase P2 from phase generator 53 and the synchronization signal from opto-electronic circuit 40 for producing an appropriately timed output corresponding to one of the twenty blocks of 8 photodiodes.

Figure 7:
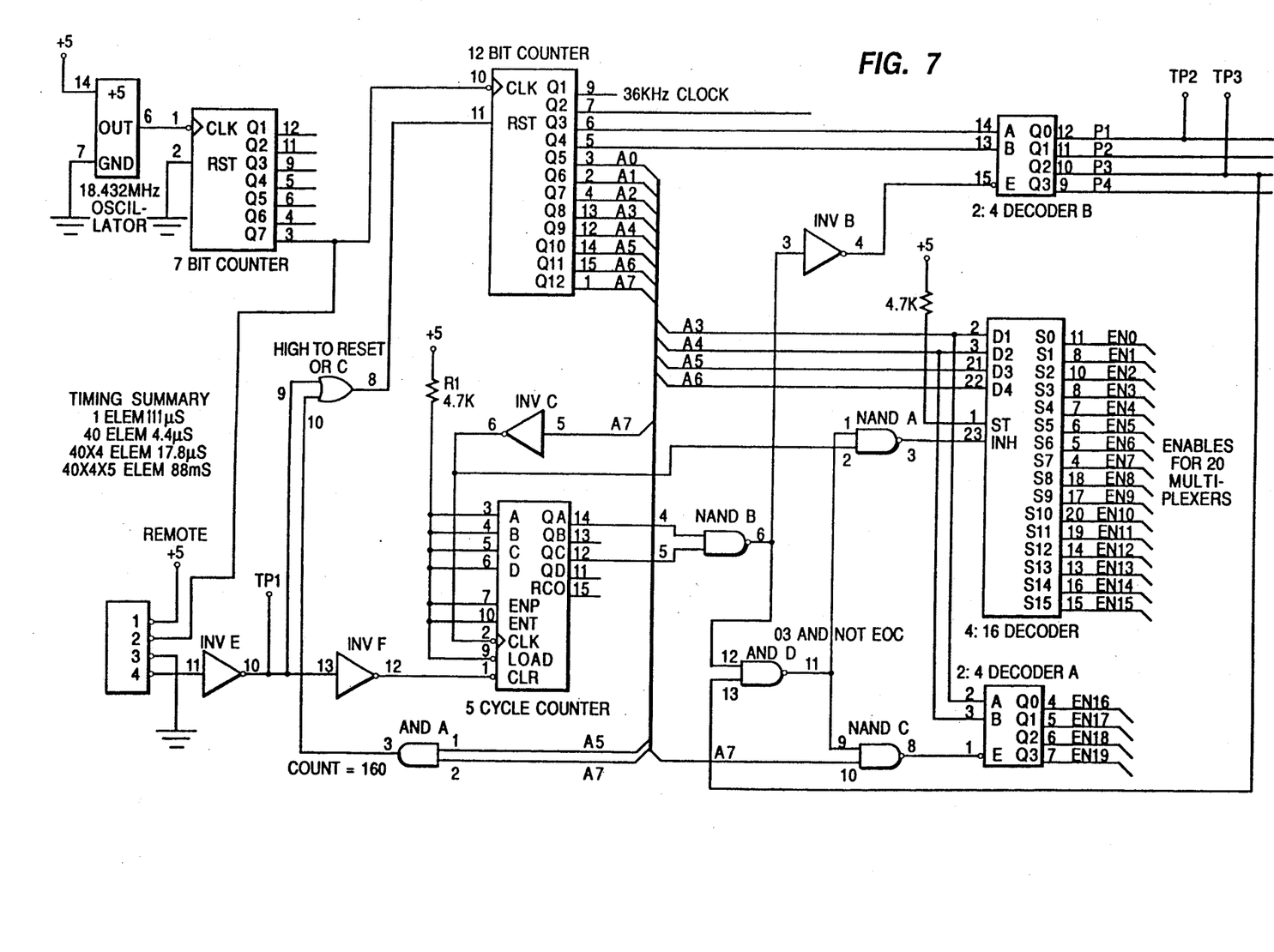
FIG. 7 is a circuit schematic of a digital control circuit for implementing portions of the scanner illustrated in FIG. 6.

A digital control circuit for performing the functions of oscillator 51, four phase generator, 53, address generator 55 and enable decoder 57 is shown in FIG. 7. For greater noise immunity and simplified design, CMOS digital logic is preferably used. An 18.432 MHz crystal provides a stable timing base for the system. A seven bit counter divides that frequency by 128 providing the base frequency of 144 KHz. The first bit of the following 12 bit counter is unused to avoid digital timing conflicts during reset. Address lines A0 to A2 of the 12 bit counter are used to select one of 8 inputs on each multiplexer 67 (see FIG. 8). Address lines A3–A6 of the 12 bit counter are decoded by a 4:16 digital decoder to produce 16 multiplexer enable signals, and a 2:4 digital decoder for producing another 4 multiplexer enable signals. Address line A7 selects which decoder, if any, is active.

Figure 8:
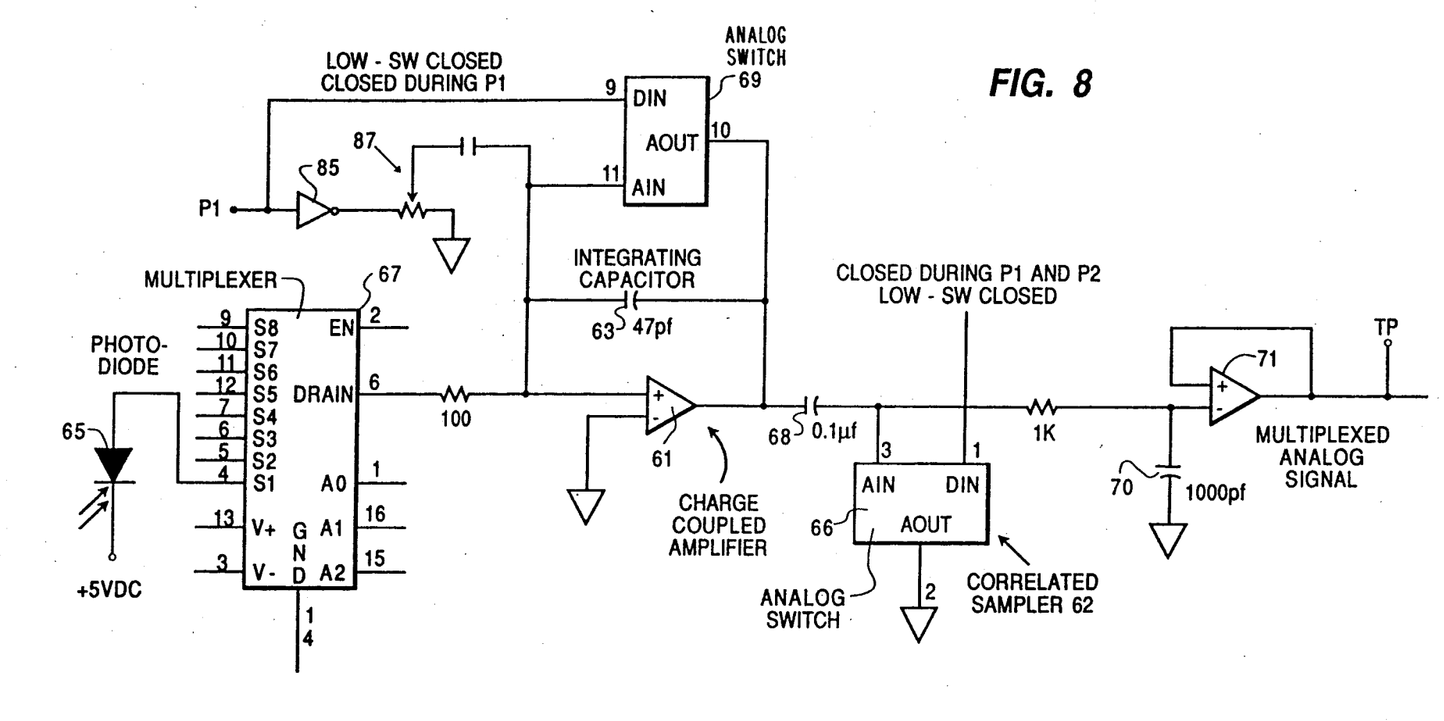
FIG. 8 is a circuit schematic illustrating one of 140 photodiodes connected via a multiplexer to an amplifier in the charge coupled mode and including a double correlated sampler.

Referring back to FIG. 6, multiplexer network 59 combines the address from address generator 55 and the enable outputs of enable decoder 57 for sequentially connecting the photodiodes to be scanned to a charge coupled amplifier 61 which is followed by a double correlated sampler 62. FIG. 8 is a circuit schematic showing a multiplexer 67, for example a Signetics, Inc. HEF 4051B multiplexer, for connecting a selected one of the photodiodes 65 to a charge coupled amplifier 61. In the present implementation, with 4 photodiode arrays, each having 35 photodiode elements, five 8:1 multiplexers are used to select an individual photodiode in one of the arrays. For ease in layout, the last five channels in the last multiplexer are unused. With 4 photodiode arrays, there are a total of 20 multiplexers in multiplexer network 59. The 20 enable signals produced by the 4:16 demultiplexer and the 2:4 demultiplexer shown in FIG. 7 are used to enable respective ones of the multiplexers in network 57. After all 4 arrays are scanned (effectively 160 elements), a reset pulse (A5 anded with A7) is used to reset the binary 12 bit counter in FIG. 7. Five different optical signals are presented to each array sequentially by shutter 17. After the fifth pass through all 160 elements, the scanning of the photodiodes is stopped while the instrument controller (not shown) absorbs the data. A separate 5 cycle counter (FIG. 7) halts the four phase clock until the next scan begins. A separate counter in the instrument controller (not shown) separately encodes all 8 address lines for storing the digitized data into 800 separate memory locations.

Figure 9:
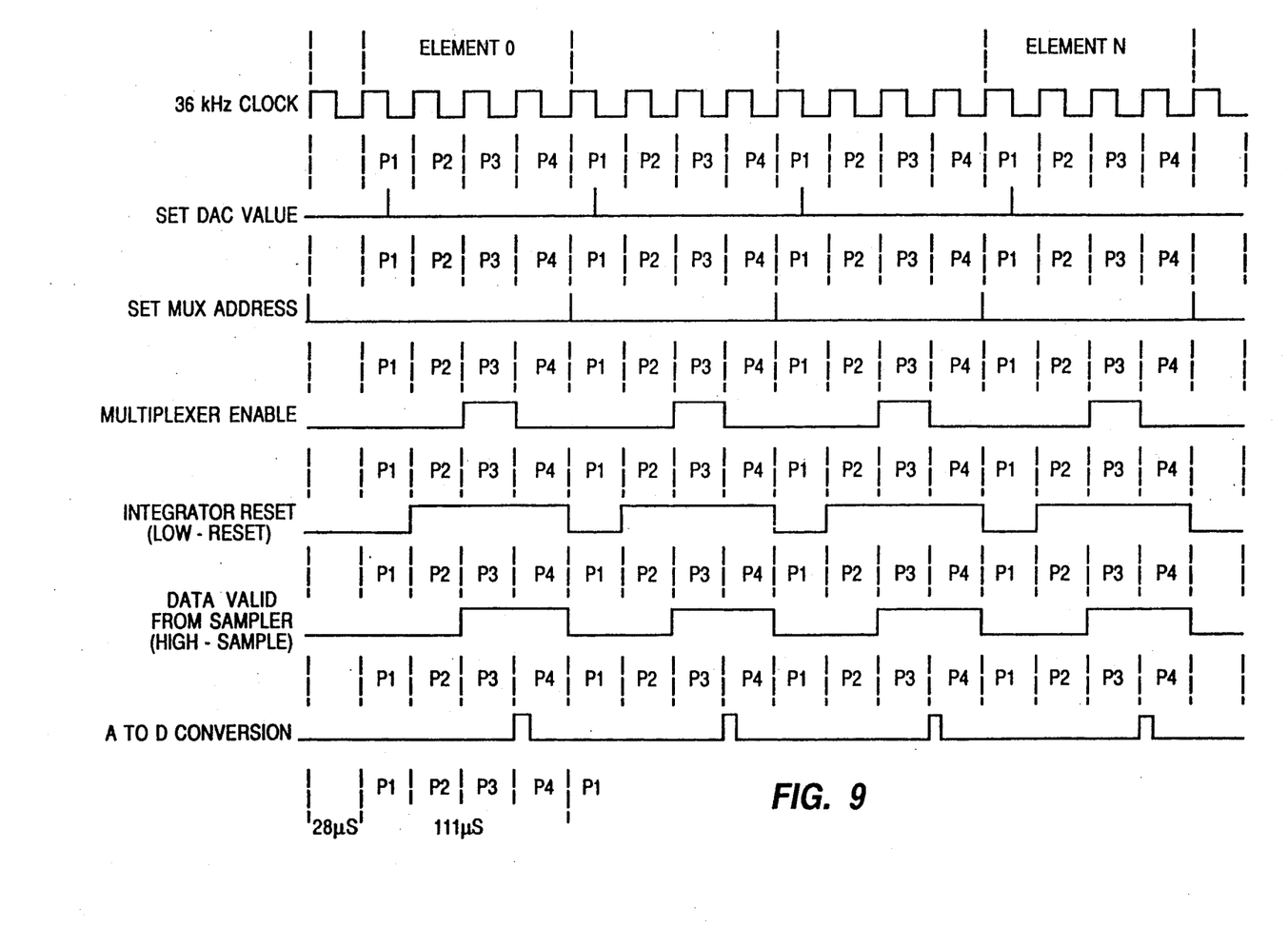
FIG. 9 is a diagram of a charge coupled amplifier timing chart showing how the phases of the four phase generator shown in FIG. 6 control the scanner electronics.

As previously noted, in the charged storage mode of operation, the amount of charge driven out of the p-n junction of the photodiode as light strikes the photodiode surface is measured by determining how much charge it takes to recharge the photodiode element. Transferring and measuring the charge required to replenish the photodiode is done by way of the phases provided by four phase generator 53 as more clearly illustrated by the charge coupled amplifier timing chart shown in FIG. 9 which summarizes the charge transfer cycle. In phase P1 the charge coupled amplifier is reset and made ready for the next charge integration. Also during phase P1 the multiplexer address is encoded to be measured. During phase P3 the multiplexer is enabled and the current path for recharging a specified photodiode is complete. During phase P3 an analog voltage proportional to the total amount of light integrated on the photodiode since the last time it was read is now available at the output of the charge coupled amplifier. The high to low transition of phase P3 is used to trigger an analog to digital converter (described below) to start a conversion for transferring data to a memory located in the instrument controller (not shown). The cycle then repeats, resetting the integrating capacitor and selecting the next multiplexer channel.

Referring again to FIG. 8, when determining the charge depleted in photodiode 65, it is the current required to recharge the diode that is actually measured. Operational amplifier 61 serves as the charge coupled amplifier. An integrating capacitor 63 across operational amplifier 61 integrates the total charge required to replenish the charge lost by photodiode 65. As photodiode 65 recharges, operational amplifier 61 attempts to hold its inverting input at a virtual ground. The amount of current required to recharge photodiode 65 integrates across integrating capacitor 63.

The output of operational amplifier 61 during phases P3 and P4 is a stepped voltage. Included in the stepped voltage are several spurious signals not related to the photodiode charge. A DC voltage level from the integrating circuitry also shows up at the charge coupled amplifier 61, making low voltage levels difficult to evaluate after amplification. These DC levels can be offset by double correlated sampling performed by correlated sampler 62 (FIG. 6), a circuit schematic of which is shown in FIG. 8. As shown in FIG. 8, an analog sampling switch 66 is closed during phases P1 and P2 (until after multiplexer 67 is set up and integrating capacitor 63 has been reset). As multiplexer 67 is enabled analog switch 66 opens. This allows a sampling capacitor 68 to sample the analog signal immediately thereafter. Effectively, only the difference between the signal after and the signal before is then passed on for further processing.

With reference to FIG. 8, charge is also injected into an integrating analog switch 69 connected across amplifier 61. Both analog switches 66 and 69 are switches with a very low charge injection (about 10pC), for example Harris, Inc. HI3-201 HS analog switches. Therefore, very little if any charge is actually injected. However, by AC coupling via an invertor 85 and an RC network 87 an inverted form of the phase P1 signal to the inverting terminal of operational amplifier 61, the effect of the charge injected is cancelled. Capacitor and resistor values of the AC coupling must be selected so that the signal coupled is equivalent to the charge injected by the original signal. The analog multiplexed signal is then filtered by a capacitor 76 to reduce high frequency noise and buffered for further processing.

The circuits described so far provide a raw analog signal. In order for the signal from the charge coupled amplifier to be meaningful, the signal is normalized, filtered, sampled, converted to digital format and then transmitted to host controller for digital processing.

Thus, the output of correlated sampler 62 is buffered by a pre-amplifier 71, the output of which is passed through a programmable amplifier 73, then to a sample and hold circuit 75, and finally to an analog to digital (A to D) converter 77. The output of A to D converter 77 is sent to the memory of the instrument controller (not shown), possibly by way of a buffer (not shown).

Figure 10:
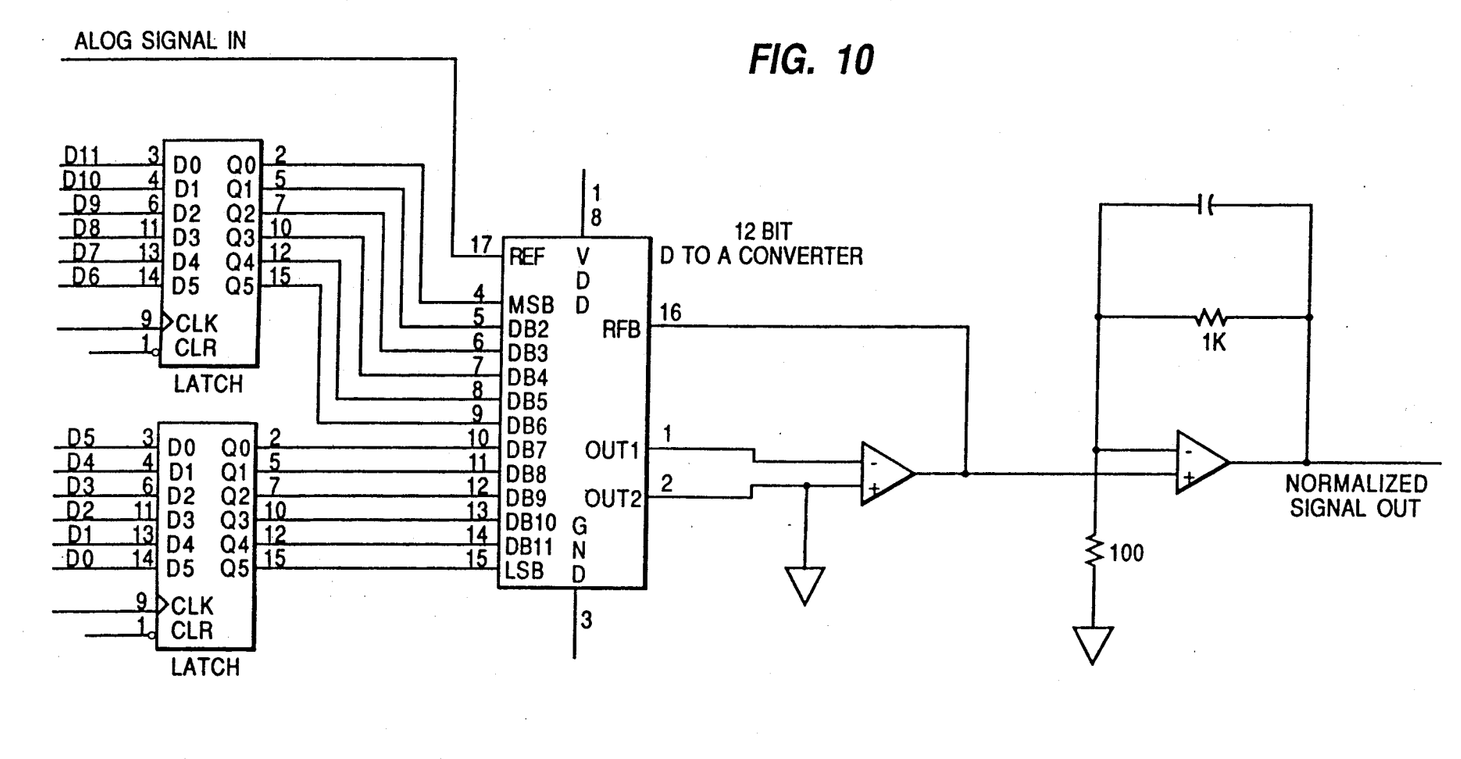
FIG. 10 is a circuit schematic of an embodiment for a programmable amplifier used in the scanner shown in FIG. 6.
Figure 11:
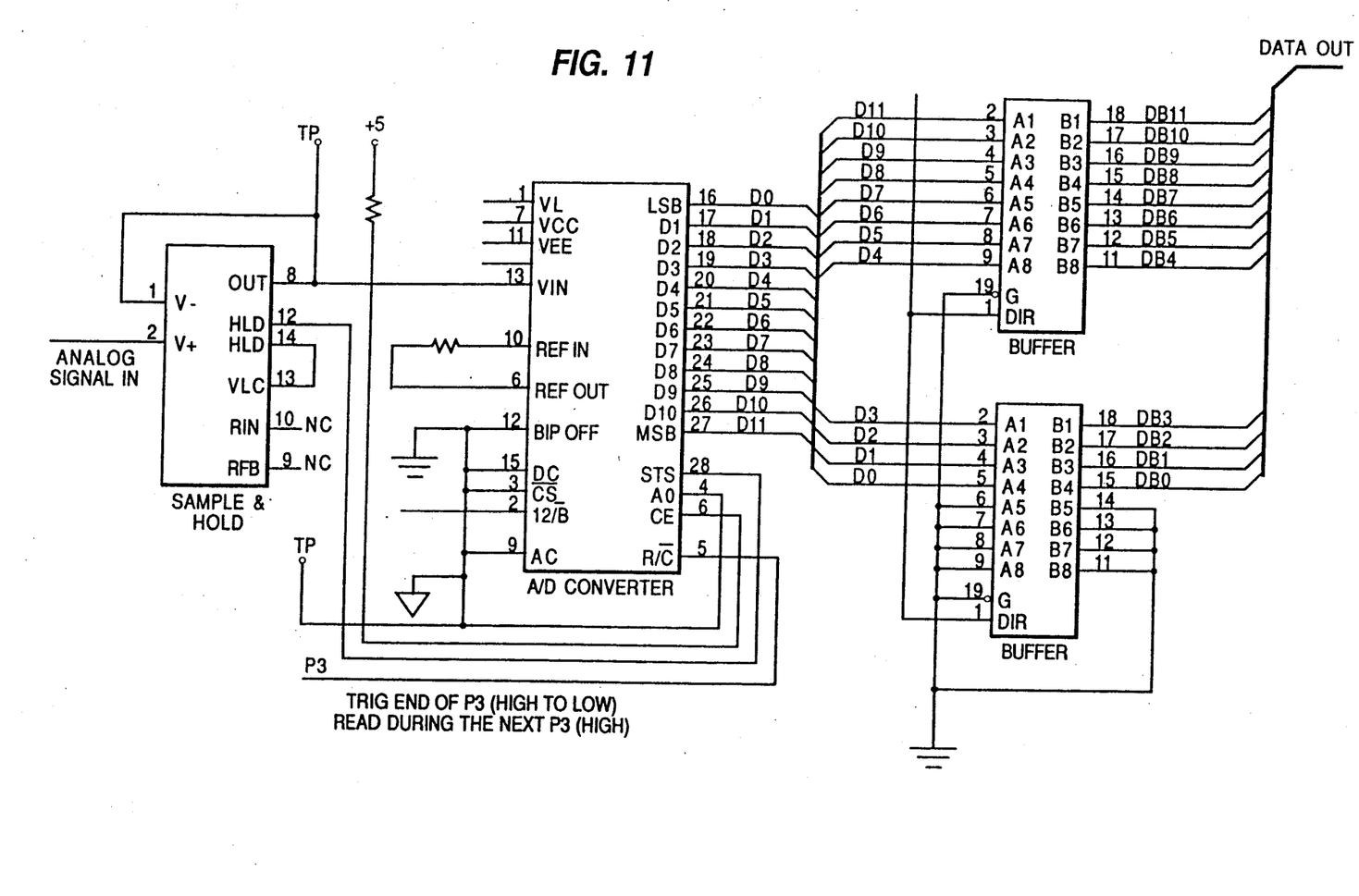
FIG. 11 is a circuit schematic of an embodiment for a sample and hold circuit and A to D converter used in the scanner of FIG. 6.

A circuit schematic for programmable amplifier 73 is shown in FIG. 10 and a circuit schematic for sample and hold circuit 75 and A to D converter 77 is shown in FIG. 11.

Proper evaluation of optical reactions requires that equivalent reactions in any optical path produce the same electrical signal regardless of which path or which photodiode is used. The electrical response must be independent of path or photodiode. Practically, all photodiodes and all optical paths cannot be made identical. However, the gain can be adjusted for each channel to compensate for these variations. In large systems of photodiode arrays, it is not practical to install a separate adjustment for each channel.

Therefore, in this system, a programmable gain amplifier 73, shown generally in FIG. 6 and in detail in FIG. 10, is used to adjust the gain of the multiplexed signal. The gain is changed each time a new photodiode channel is selected.

Referring to FIG. 10, a 12 bit Digital to Analog converter (DAC), for example a PMI PM 7541A DAC, is used so that one of 4095 discrete gain values can be selected. An amplifier following the D to A converter sets the range of the gain. In this case the maximum gain is 100.

The instrument controller sets the gain value at a time that digital noise will not influence the analog signal. In this circuit phase Pl is chosen to set up the value on data latches, which may be TTL 74 LS 174 latches. Half way through phase Pl, the data are stored into the latches.

In order for the gain to be set appropriately for each channel, the controller must have a method for determining what the gain should be to normalize all channels. First, a reference material is placed in each optical path (usually water). Then a normalization value is selected. One scan of the photodiode array must occur for each bit of the D to A converter starting with the highest bit. The high bit is set to logic level 1 (DAC value = 2048). If after the first scan the signal received is higher than the requested normalized value then the high bit is reset for that channel (value = 0); otherwise, the high bit remains at 1 for that channel. Progressing through the remaining 11 bits in like manner produces a table of values between 0 and 4095 corresponding to the required gain for each optical path and photodiode for normalizing the gain from channel to channel.

The final gain for any one element is:

$$\text{GAIN} = \frac{DAC \text{ VALUE}}{(2 \text{ NUMBER OF BITS})} \times \text{GAIN OF } OP \text{ } AMP$$

For this system the gain is $$\text{GAIN} = \frac{VAC \text{ VALUE}}{4095} \times 100$$

Although the analog signal is considered to be valid during phase P3 and P4, it will vary with phase switching noise and signal decay. To improve accuracy from scan to scan, a sample and hold circuit 75, for example an Analog Devices AD 585, is included before A to D converter 77, both shown generally in FIG. 6 and in detail in FIG. 11. The A to D convertor may be an Analog Devices AD 574. The high to low transition of phase P3 starts a conversion by the A to D converter. The converter status line goes low, switching the sample and hold circuit from sample to hold. Thus the conversion takes place at the same point in time (the end of phase P3) each scan.

Data buffers are preferably used to improve transportation of the digital signal to and from the controller. Digitally converted data are read by the controller during the next phase P3 (R/C high on the A to D converter) and the direction line (DIR) high on the buffer. D to A values for the programmable gain amplifier are written by the controller during phase Pl (DIR low on the buffer).

In operation, a sampling handling system continuously feeds a linear stream of cuvettes into the optical paths of the divided beams as shown in FIG. 1. Each cuvette has a plurality of linearly arranged reaction wells, each of which contains a reaction volume whose optical characteristics are to be monitored. The sample handling system moves the cuvettes an incremental distance corresponding to the width of one reaction well periodically, say every 15 seconds. This motion is preferably accomplished in 0.1 seconds. Shutter 17 sequentially passes all 20 of the beams transmitted by the 20 reaction wells in a total of 0.1 seconds, but as previously described, shutter 17 allows only one beam of each group of five beams to reach a respective one of the four photodiode arrays 23 at any one instant of time. The optical path of each of the 20 beams represents a measuring station. With a total of 20 stations, and if each reaction well remains in a station for 15 seconds, and a spectral distribution from each reaction volume falls on a 35 element array 10 times per second, a total of 7000 discrete optical signals are recorded each second (i.e. 350 discrete optical signals per second per station). Since each reaction well remains in a station for 15 seconds, and there are 20 stations, the reaction volume in each reaction well is optically monitored for 300 seconds by the time it moves out of the last station. When the trailing reaction well of a cuvette leaves the last station, the cuvette is guided along the track to a waste container for disposal.

The rapid scanning achievable by the optical monitoring system according to the invention makes it possible to select the wavelength at which the optical transmission for each test is to be monitored. Wavelength selection can take place in less than 0.1 seconds after the sample and additives are added to the reaction well to form a reaction volume and before the reaction is fully underway. By selecting the wavelength, the reaction volume can be optically monitored under optimum conditions. For example, a balance between signal to noise and sensitivity can be achieved for a clotting test by selecting the shortest wavelength for which the signal just exceeds a preset threshold. That is, it has been observed that optical transmission of a sample shows a greater change during clotting reactions for shorter wavelength light than for longer wavelength light. A second observation is that there is less overall light transmitted at shorter wavelengths than at longer wavelengths. Therefore, the reactions should be observed at the shortest wavelength for which there is adequate signal (versus noise) in order to achieve the optimum overall sensitivity.

With the optical monitoring system according to the invention, the photodiode arrays can be electronically scanned from the short wavelengths towards the long wavelengths. The first photodiode element encountered that has a signal above a predetermined threshold value is designated as the element (wavelength) at which to monitor the reaction volume. This selection process, as noted above, takes place immediately upon addition of the reagent to the sample volume prior to any significant reaction occurring. With the optimum wavelength selected in this fashion, there is no need to acquire, store or process data generated by other photodiode elements in the array. It should be clear to those skilled in the art that other criteria for selecting a predetermined threshold can be employed for selecting the particular photodiode element to monitor.

Obviously, numerous and additional modifications and variations of the present invention are possible in light of the above teachings. It is therefore to be understood that within the scope of the appended claims, the invention may be practiced otherwise than as specifically claimed.

What is claimed is:

1. A multichannel optical monitoring system for monitoring the spectral transmission of a plurality of samples, comprising:
   beam means for generating a plurality of light beams;

a plurality of optical monitoring stations arranged one after the other along a pathway, each station having an optical path formed by one of the light beams transverse to said pathway and along which optical characteristics are monitored;

drive means for moving a plurality of reaction wells, each containing a reaction volume, along said pathway from station to station so that respective reaction volumes dwell periodically in each optical path for transmitting a respective one of the light beams;

diffraction means arranged for diffracting the beams transmitted by respective ones of the reaction volumes;

focusing means following said diffraction means for focussing the diffracted beams;

at least one array of photodetectors positioned for receiving the beams diffracted by said diffraction means and focussed by said focussing means for producing electrical signals representing the spectral content of the diffracted beams;

shutter means disposed in the optical pathways formed by the light beams between said beam means and said diffraction means for sequentially passing the light beams toward said diffraction means; and electronic means for detecting the electrical signals of said at least on array.

2. A monitoring system as defined in claim 1, wherein said shutter means comprises a rotating cylinder defining radial passages axially arranged for sequentially passing the light beam.

3. A monitoring system as defined in claim 2, wherein said rotating cylinder includes a plurality of concentrically arranged discs each having a sector removed for defining the respective radial passages.

4. A monitoring system as defined in claim 1, wherein said at least one array comprises a plurality of arrays, each array being associated with a group of beams; and said shutter means sequentially passes the beams in each group so that only one light beam of each group of beams is allowed to reach a respective one of the arrays at any one time.

5. A monitoring system as defined in claim 1, wherein said shutter means is disposed between said pathway and said diffraction means.

6. A multichannel optical monitoring system for monitoring the spectral transmission of a plurality of samples, comprising:

a broad spectral band light source;

slit means defining a slit positioned in front of said light source for passing a light beam having the pattern of the slit;

collimating means following said slit means for projecting the light beam to infinity to form a diverging beam;

beam dividing means following said collimating means for dividing the diverging beam into a number of spaced apart light beams;

a plurality of optical monitoring stations arranged one after the other along a pathway, each station having an optical path formed by one of the spaced apart light beams transverse to said pathway and along which optical characteristics are monitored;

drive means for moving a plurality of reaction wells, each containing a reaction volume, along said pathway from station to station so that respective reaction volumes dwell periodically in each optical path for transmitting a respective one of the spaced apart light beams;

diffraction means arranged for diffracting the beams transmitted by respective ones of the reaction volumes;

focusing means following said diffraction means for focussing the diffracted beams;

at least one array of photodetectors positioned for receiving the beams diffracted by said diffraction means and focussed by said focussing means for producing electrical signals representing the spectral content of the diffracted beams; and electronic means for detecting the electrical signals of said at least one array.

7. A monitoring system as defined in claim 6, wherein said beam dividing means comprises a mask with linearly arranged openings so that each light beam passes through a respective one of the reaction volumes.

8. A monitoring system as defined in claim 6, and further comprising filter means following said collimating means for balancing the spectral response of the said array of photodetectors with said light source.

9. A monitoring system as defined in claim 6, and further including at least one mirror in the path of said light beam for folding the light beam.

10. A multichannel optical monitoring system for monitoring the spectral transmission of a plurality of samples, comprising:

beam means including a light source and defining a slit through which light from said source is passed having a pattern of said slit and for generating a plurality of light beams from the light passed through said slit;

a plurality of optical monitoring stations arranged one after the other along a pathway, each station having an optical path formed by one of the light beams transverse to said pathway and along which optical characteristics are monitored;

drive means for moving a plurality of reaction wells, each containing a reaction volume, along said pathway from station to station so that respective reaction volumes dwell periodically in each optical path for transmitting a respective one of the light beams;

diffraction means arranged for diffracting the beams transmitted by respective ones of the reaction volumes;

focusing means following said diffraction means for focussing the diffracted beams;

at least one linear array of photodetecting elements positioned for receiving the beams diffracted by said diffraction means and focussed by said focussing means for producing electrical signals representing the spectral content of the diffracted beams, said array having a central element which is the optical conjugate of said slit; and electronic means for detecting the electrical signals of said at least one array.

11. A monitoring system as defined in claim 10, wherein said light source comprises a tungsten-halogen lamp.

12. A monitoring system as defined in claim 10, wherein said light source comprises a xenon lamp.

13. A monitoring system as defined in claim 10, wherein said diffraction means comprises a diffraction grating.

14. A monitoring system as defined in claim 10, wherein said diffraction means comprises a holographic diffraction grating.

15. A monitoring system as defined in claim 10, wherein said array is oriented so that the diffracted light beam falls across the elements of said array.

16. A monitoring system as defined in claim 10, wherein said photodetecting elements comprise photodiodes.

17. A monitoring system as defined in claim 10, wherein said electronic means includes programmable gain means for adjusting the gain of each detected electrical signal.

18. A monitoring system as defined in claim 10, wherein said diffraction means, said focussing means and said array are arranged to produce a spectral resolution of at least 10 nm in a spectral range of at least 390 nm to 690 nm.

19. A monitoring system as defined in claim 10, wherein said focusing means comprises at least one lens following said diffraction means.

20. A monitoring system as defined in claim 10, wherein said electronic means is based on the charge storage mode of operation.

21. A monitoring system as defined in claim 10, wherein said pathway is a linear pathway.

22. A method for monitoring the spectral transmission of a plurality of samples, comprising:
providing a light source;
passing light from the light source through a slit;
generating a plurality of light beams from the light passing through the slit;
arranging a plurality of optical monitoring stations along a pathway, each station having an optical path formed by one of the light beams transverse to the pathway and along which optical characteristics are monitored;
moving a plurality of reaction wells, each containing a reaction volume, along the pathway from station to station so that respective reaction volumes dwell periodically in each optical path for transmitting a respective one of the light beams;
diffracting the beams transmitted by respective ones of the reaction volumes;
focussing the diffracted beams onto a linear array of photodetecting elements having a central element which is the optical conjugate of the slit;
converting the diffracted and focussed beams, by way of the linear array, to electrical signals representing the spectral content of the diffracted beams; and
detecting the electrical signals.

23. A method as defined in claim 22, and further comprising the step of sequentially passing the light beams.

24. A method as defined in claim 22, wherein said converting step includes arranging the array so that the diffracted light beam falls across the elements of the array.

25. A method for monitoring the spectral transmission of a plurality of samples, comprising:
generating a plurality of light beams;
arranging a plurality of optical monitoring stations along a pathway, each station having an optical path formed by one of the light beams transverse to the pathway and along which optical characteristics are monitored;
moving a plurality of reaction wells, each containing a reaction volume, along the pathway from station to station so that respective reaction volumes dwell periodically in each optical path for transmitting a respective one of the light beams;
diffracting the beams transmitted by respective ones of the reaction volumes;
focussing the diffracted beams;
converting the diffracted and focussed beams to electrical signals representing the spectral content of the diffracted beams with the use of an array of photodetecting elements; and
detecting the electrical signals, wherein said detecting step includes scanning the array of photodetecting elements to determine the photodetecting element which produces an electrical signal which exceeds a predetermined threshold and thereafter detecting only the electrical signal from that photodetecting element.

26. A method for monitoring the spectral transmission of a plurality of samples, comprising:
generating a plurality of light beams;
arranging a plurality of optical monitoring stations along a pathway, each station having an optical path formed by one of the light beams transverse to the pathway and along which optical characteristics are monitored;
moving a plurality of reaction wells, each containing a reaction volume, along the pathway from station to station so that respective reaction volumes dwell periodically in each optical path for transmitting a respective one of the light beams;
diffracting the beams transmitted by respective ones of the reaction volumes;
focussing the diffracted beams;
converting the diffracted and focussed beams to electrical signals representing the spectral content of the diffracted beams with the use of an array of photodetecting elements; and
detecting the electrical signals, wherein said detecting step includes the step of adjusting the gain of the electrical signal detected from each photodetecting element.

27. A multichannel optical monitoring system for monitoring the spectral transmission of a plurality of samples, comprising:
beam means for generating a plurality of light beams;
a plurality of optical monitoring stations arranged one after the other along a pathway, each station having an optical path formed by one of the light beams transverse to said pathway and along which optical characteristics are monitored;
drive means for moving a plurality of reaction wells, each containing a reaction volume, along said pathway from station to station so that respective reaction volumes dwell periodically in each optical path for transmitting a respective one of the light beams;
diffraction means arranged for diffracting the beams transmitted by respective ones of the reaction volumes;
focusing means following said diffraction means for focussing the diffracted beams;
at least one linear array of photodetecting elements positioned for receiving the beams diffracted by said diffraction means and focussed by said focussing means for producing electrical signals representing the spectral content of the diffracted beams; and electronic means for detecting the electrical signals of said at least one array, said electronic means including programmable gain means for adjusting the gain of each detected electrical signal.

28. A multichannel optical monitoring system for monitoring the spectral transmission of a plurality of samples, comprising:

beam means for generating a plurality of light beams;

a plurality of optical monitoring stations arranged one after the other along a pathway, each station having an optical path formed by one of the light beams transverse to said pathway and along which optical characteristics are monitored;

drive means for moving a plurality of reaction wells, each containing a reaction volume, along said pathway from station to station so that respective reaction volumes dwell periodically in each optical path for transmitting a respective one of the light beams;

diffraction means arranged for diffracting the beams transmitted by respective ones of the reaction volumes;

focusing means following said diffraction means for focussing the diffracted beams;

at least one array of photodetectors positioned for receiving the beams diffracted by said diffraction means and focussed by said focussing means for producing electrical signals representing the spectral content of the diffracted beams; and electronic means for detecting the electrical signals of said at least one array, wherein said diffraction means, said focussing means and said array are arranged to produce a spectral resolution of at least 10 nm in a spectral range of at least 390 nm to 690 nm.

29. A multichannel optical monitoring system for monitoring the spectral transmission of a plurality of samples, comprising:

beam means for generating a plurality of light beams;

a plurality of optical monitoring stations arranged one after the other along a pathway, each station having an optical path formed by one of the light beams transverse to said pathway and along which optical characteristics are monitored;

drive means for moving a plurality of reaction wells, each containing a reaction volume, along said pathway from station to station so that respective reaction volumes dwell periodically in each optical path for transmitting a respective one of the light beams;

diffraction means arranged for diffracting the beams transmitted by respective ones of the reaction volumes;

focusing means including at least one lens following said diffraction means for focussing the diffracted beams;

at least one array of photodetectors positioned for receiving the beams diffracted by said diffraction means and focussed by said focussing means for producing electrical signals representing the spectral content of the diffracted beams; and electronic means for detecting the electrical signals of said at least one array.

30. A multichannel optical monitoring system for monitoring the spectral transmission of a plurality of samples, comprising:

beam means for generating a plurality of light beams;

a plurality of optical monitoring stations arranged one after the other along a pathway, each station having an optical path formed by one of the light beams transverse to said pathway and along which optical characteristics are monitored;

drive means for moving a plurality of reaction wells, each containing a reaction volume, along said pathway from station to station so that respective reaction volumes dwell periodically in each optical path for transmitting a respective one of the light beams;

diffraction means arranged for diffracting the beams transmitted by respective ones of the reaction volumes;

focusing means following said diffraction means for focussing the diffracted beams;

at least one array of photodetectors positioned for receiving the beams diffracted by said diffraction means and focussed by said focussing means for producing electrical signals representing the spectral content of the diffracted beams; and electronic means, based upon the charge storage mode of operation, for detecting the electrical signals of said at least one array.

* * * * *